United States Patent
Byrne (10) Patent No.: US 11,752,363 B2
(45) Date of Patent: Sep. 12, 2023

(54) RADIOTHERAPY APPARATUS WITH CALIBRATION

(71) Applicant: Elekta Limited, West Sussex (GB)

(72) Inventor: Julian Byrne, Shore-ham-by-Sea (GB)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 16/604,904

(22) PCT Filed: Mar. 27, 2018

(86) PCT No.: PCT/EP2018/057812
§ 371 (c)(1),
(2) Date: Oct. 11, 2019

(87) PCT Pub. No.: WO2018/188949
PCT Pub. Date: Oct. 18, 2018

(65) Prior Publication Data
US 2020/0384291 A1    Dec. 10, 2020

(30) Foreign Application Priority Data

Apr. 11, 2017 (GB) ..................................... 1705865

(51) Int. Cl.
*A61N 5/10* (2006.01)
*A61B 6/04* (2006.01)
*A61B 6/00* (2006.01)

(52) U.S. Cl.
CPC .......... *A61N 5/1075* (2013.01); *A61B 6/0407* (2013.01); *A61B 6/583* (2013.01);
(Continued)

(58) Field of Classification Search
CPC ................ A61N 5/1075; A61N 5/1049; A61N 2005/1054; A61N 2005/1055;
(Continued)

(56) References Cited

U.S. PATENT DOCUMENTS 4,233,507 A    11/1980  Volz
5,537,452 A *   7/1996  Shepherd ............... A61N 5/103
                                                378/65
(Continued)

FOREIGN PATENT DOCUMENTS

EP          2865418 A1    4/2015
WO     WO-2018188949 A1  10/2018

OTHER PUBLICATIONS

"International Application No. PCT/EP2018/057812, International Search Report and Written Opinion dated Jul. 11, 2018", (Jul. 11, 2018), 11 pgs.

(Continued)

*Primary Examiner* — David P Porta
*Assistant Examiner* — Mamadou Faye
(74) *Attorney, Agent, or Firm* — Schwegman Lundberg & Woessner, P.A.

(57) ABSTRACT

A radiotherapy apparatus is disclosed, having an imaging system and a therapeutic radiation source, an imageable volume into which therapeutic radiation may be provided, a first imaging means for providing an image resulting from the imaging system and a second imaging means for providing an image resulting from the therapeutic radiation, and a patient support moveable relative to the volume, wherein the patient support is provided with a calibration portion comprising at least one object of a material capable of appearing in the image produced by the first imaging means and at least one object of a material capable of appearing in the image produced by the second imaging means, the at least one object being fixed in a pre-determined position relative to the calibration portion and the calibration portion being fixed in a pre-determined position relative to the patient support, the patient support being moveable so that (Continued)

the at least one object portion may optionally be positioned within or outside the volume.

18 Claims, 5 Drawing Sheets

(52) U.S. Cl.
CPC .... *A61N 5/1049* (2013.01); *A61N 2005/1054* (2013.01); *A61N 2005/1055* (2013.01); *A61N 2005/1076* (2013.01)

(58) Field of Classification Search
CPC .......... A61N 2005/1076; A61B 6/0407; A61B 6/583; A61B 6/04
See application file for complete search history.

(56) References Cited

U.S. PATENT DOCUMENTS

| | | | | |
|---|---|---|---|---|
| 6,282,264 | B1* | 8/2001 | Smith | A61B 6/4233 378/189 |
| 8,186,880 | B1 | 5/2012 | Arnold | |
| 8,915,833 | B1* | 12/2014 | Sahadevan | A61N 5/1084 600/1 |
| 2005/0234327 | A1 | 10/2005 | Henderson et al. | |
| 2007/0296576 | A1* | 12/2007 | Holowick | G01R 33/28 340/539.21 |
| 2008/0118103 | A1* | 5/2008 | Pescatore | A61B 34/20 382/103 |
| 2012/0265050 | A1* | 10/2012 | Wang | A61B 5/0035 600/411 |
| 2013/0235969 | A1* | 9/2013 | Winter | A61B 6/5247 378/4 |
| 2013/0317343 | A1* | 11/2013 | Klimenko | A61N 5/1039 600/411 |
| 2015/0230766 | A1* | 8/2015 | Wang | A61B 6/037 600/411 |
| 2016/0023019 | A1 | 1/2016 | Filiberti et al. | |
| 2016/0129283 | A1* | 5/2016 | Meir | G06T 7/85 348/46 |
| 2017/0046856 | A1 | 2/2017 | Hirai et al. | |
| 2019/0156525 | A1* | 5/2019 | Liu | A61B 6/4429 |

OTHER PUBLICATIONS

"United Kingdom Application GB1705865.2, UKIPO Search Report dated Oct. 16, 2017", (Oct. 16, 2017), 3 pgs.

* cited by examiner

RADIOTHERAPY APPARATUS WITH CALIBRATION

This is a U.S. National Stage Patent Application which claims priority to Application Serial No. PCT/EP2018/057812, filed Mar. 27, 2018, and published on Oct. 18, 2018 as WO 2018/188949 A1, which claims the benefit of priority to GB Application Serial Number 1705865.2, filed Apr. 11, 2017, which are hereby incorporated by reference in their entirety.

FIELD OF THE INVENTION

The present application relates to radiotherapeutic apparatus, and especially to such apparatus in which imaging and therapy of a patient may take place during a single session— for example during a treatment fraction.

BACKGROUND ART

A well-known challenge in the radiotherapy field is that patients and parts of their body can move over time. This is usually involuntary, due to the normal cardio-vascular cycle and related internal movements. In radiotherapy it is highly desirable to ensure that a radiation dose is delivered to the right location for treatment, and that radiation delivery to other locations is minimised as far as possible to avoid unwanted effects.

To that end radiotherapeutic apparatus may have both an imaging system as well as a treatment system. Thus, the precise location of organs for example may be determined at or shortly before radiation treatment begins or even during the treatment fraction itself so that a pre-determined treatment plan can be updated accordingly.

However, calibration of the apparatus is important, as the imaging and treatment delivery systems may operate according to different principles or may be not precisely co-located. For example, X-ray imaging systems (such as portal imaging systems) generally have a spatially fixed frame of reference resulting from the location of the radiation source and the detector. The frame of reference can drift over time as the apparatus is used, but this is generally a slow process. MRI imaging systems do however have a frame of reference that is less rigidly fixed to the physical apparatus, and can vary as the spatial configuration of local ferromagnetic and other objects varies. Thus, regular calibration is especially useful where X-ray and MRI systems are combined and need to be cross-referenced.

U.S. Pat. No. 4,233,507 of Volz discloses a table top for a computed tomography (CT) imaging device. The table top disclosed includes a sample of reference material which is visible in each CT image and can thus be used to calibrate the system. However, the Volz disclosure is mainly aimed at overcoming known challenges of CT imaging related to calibrating the various contrast levels of different materials with different X-ray attenuation properties, rather than spatial calibration which is the subject of the present invention.

U.S. Pat. No. 8,186,880 of Arnold is a development of the Volz concept, aimed at determining tissue properties in the body of a subject. Arnold discloses a couch pad, patient support or table top having samples and targets of a variety of reference materials permanently enclosed within. The reference materials are homogenous and of sufficient length to always be present in the image for all torso exams. Thus, any body part can be post-analysed by comparison between the image densities of the tissue and the known reference materials. Again, Arnold is not directed to location calibration, differentiating it from the present invention.

EP 2865418 of Elekta AB discloses a system in which one or more markers are provided within an imaging volume, the markers being visible to a magnetic resonance (MR) scanner or computed tomography (CT) scanner depending on which imaging technique is used. The aim of that invention is to avoid treatment radiation interacting with sensitive parts of a radiotherapy apparatus, by providing information on the location of such sensitive parts to a treatment planning system.

None of the aforementioned documents relate to the desired location calibration between imaging and treatment delivery systems. Furthermore, some disclosures require the placement of materials within the imaging volume which are likely to interfere with treatment radiation. It is desirable to minimise the presence of materials which could interact with treatment radiation, as radiation that impinges onto those materials may be scattered to patient tissue which is not intended to be irradiated; or such interference may reduce the accuracy of a radiation dosage measurement, for example by scattering, leading to errors in portal imaging.

One technique for location calibration is to provide a "phantom" having properties suitable to aid calibration such as by providing known materials in known locations relative to the phantom; these properties are sometimes similar to parts of a patient. Such a phantom may be placed on a patient support of a radiotherapy apparatus in a location similar to that which would be used by a patient. The phantom could then be subjected to imaging and treatment radiation and the results from the imaging system and—for example—portal imaging of the remaining treatment radiation could then be used along with the known characteristics of the phantom to provide calibration data. The calibration data could subsequently be used to make any required adjustments to the imaging and treatment systems. The phantom would usually subsequently be removed so that the apparatus can be used for patient treatment.

However, while such a technique can provide useful calibration it is time-consuming and resource-intensive. In a typical hospital or clinic, such calibration may be effected on a daily basis. Thus, if calibration is started at the beginning of a working day, by the time the calibration steps have been completed including any time required for computation of the results of imaging and treatment data and any required adjustments have been made, then the time available to use the apparatus for patient treatment before the end of a working day will have been reduced.

Such reduction in available treatment time could be compounded by the need for skilled technicians to be present to set up the apparatus including a phantom process the results, and then remove the apparatus from the machine before any treatments can commence. During any calibration and computation time the apparatus ought not to be used for treatment, and potentially the technicians could be idle.

SUMMARY OF THE INVENTION

Thus, it is an aim of the present invention to provide a radiotherapy apparatus including imaging and radiotherapy systems in which regular spatial calibration takes place more efficiently.

Accordingly, the present invention is directed to a radiotherapy apparatus, comprising a source of therapeutic radiation and a diagnostic imaging system, both directed toward a common volume, a portal imaging system for the therapeutic radiation, a patient table including a calibration portion integrated in the table and located at or towards one end of the patient table, and a control unit, wherein the calibration portion is resolvable in both the diagnostic imaging system and the portal imaging system and is fixed in a pre-determined position relative to the patient support, the patient table is moveable relative to the common volume to an extent sufficient to bring the calibration portion selectively into and out of the common volume, and the control unit is arranged to periodically initiate a calibration process comprising at least the steps of moving the patient table to a position in which the calibration portion is within the common volume, and obtaining an image from both the diagnostic imaging system and the portal imaging system.

Thus, during a calibration phase the calibration portion may be positioned so that it is within the volume and will thus appear on the images produced by the first and second imaging means. Such a position and such imaging enables a calculation of the relative frames of reference of the imaging system and therapeutic radiation sources, which can be used to calibrate them spatially so that they can be operated according to a common spatial reference.

During a subsequent treatment process the calibration portion may be positioned so that it lies outside the volume, and hence does not interfere with either the imaging process or the treatment radiation.

The calibration portion is integral with the patient table, and can include at least one resolvable object, which may be a single object or more than one object. Suitable materials for the object may be selected according to the type of imaging system and therapeutic radiation being used. Where there is more than one object, this may include at least one object of a material capable of appearing in the image produced by the diagnostic imaging system, and at least one object of a material capable of appearing in the image produced by the portal imaging system, the at least one objects being fixed in a pre-determined position relative to the calibration portion.

Preferably the patient support (and thus the calibration portion) is arranged in a pre-determined position during the calibration phase. This enables the calculation to take into account the known position of the calibration portion, and thus provide a more precise calculation of the relative positions of the imaging and therapeutic radiation sources.

The calibration portion is located at or towards one end of the patient support. A large remaining proportion of the patient support may thus be within the volume at other times. With the calibration portion located towards one end, the patient support can be moved so that during calibration that one end is within the imaging volume, whereas during treatment, the radiotherapy target is substantially central to the imaging volume and the calibration portion is away from the imaging/treatment region.

The control unit can further comprise a module for connection to an outside communication network. An override module can also be connected to the control unit, as can one or more monitoring devices.

The radiotherapy apparatus is preferably installed within a room, having a security system comprising at least one door connected to a locking arrangement, wherein the security system is adapted to set the locking arrangement to allow or deny access to the room. The security system can be connected to the controller of the radiotherapy apparatus. The monitoring devices can provide information about one or more conditions of the radiotherapy apparatus and/or the room.

The diagnostic imaging system is suitably a magnetic-resonance imaging ("MRI") system.

The present invention also provides a method of calibrating a radiotherapy apparatus comprising a source of therapeutic radiation and a diagnostic imaging system directed toward a common volume, a portal imaging system for the therapeutic radiation, and a patient table including a calibration portion (integrated in the table, and located at or towards one end of the patient table) that is resolvable in both the diagnostic imaging system and the portal imaging system and is fixed in a pre-determined position relative to the patient support, the calibration method comprising the steps of (i) moving the patient table relative to the common volume to an extent sufficient to place the calibration portion within the common volume, (ii) obtaining an image from both the diagnostic imaging system and the portal imaging system, (iii) spatially correlating the diagnostic imaging system and the portal imaging system on the basis of the respective images, and (iv) moving the patient table relative to the common volume to an extent sufficient to place the calibration portion outside the common volume.

A control unit may be adapted to carry out the step of calculating the position of the calibration portion relative to the imaging system and the treatment radiation source using the information from the diagnostic imaging system and the portal imaging system. The result of the calculation step may be provided to a treatment planning system. Alternatively, the result of the calculation step may be provided to a technician who may subsequently make any adjustments to the apparatus which may be required.

The step of moving the patient table relative to the common volume to an extent sufficient to place the calibration portion within the common volume can comprise moving the patient table to a pre-determined position.

As mentioned above, calibration of a radiotherapy apparatus may take up valuable time during a working day of a technician or clinician. To this end, a control unit is ideally provided, which can further comprise a module for connection to an outside communication network, such as a computer network or telephone network or the like. This can be adapted to carry out a method comprising the steps of (a) receiving an activation signal from a remote communication device, (b) carrying out safety checks, (c) performing steps (i) to (iv) above; and (d) providing a confirmation signal to a remote communication device. Thus, the radiotherapy apparatus may be calibrated ahead of the usual start of the working day, for example, thereby minimising idle time for relevant staff.

An override step can be allowed for, to bring the calibration steps to a halt and deactivate the imaging and/or therapeutic radiation source.

For example, if a technician is aware that a first patient appointment of the day is at a particular time the technician may trigger the calibration process via a mobile device before arriving at the hospital or clinic. If the calibration process is triggered at an appropriate time, the result of the calculation step may be available at the start of the working day to enable any adjustments to be made promptly. This should improve the productivity of the radiotherapy apparatus.

Alternatively, steps (b) and (c) could be scheduled, for example to take place at a pre-determined time of day.

If calibration is to be effected without the presence of a suitably qualified person then it is important that the room housing the radiotherapy apparatus is in a suitable state before the calibration steps begin. For example, MR devices utilise powerful electromagnets and therefore during operation it is important to ensure that there are no ferromagnetic objects in the vicinity of the MR device. Similarly, radiotherapy apparatus often utilise ionising radiation. While such ionising radiation is generally collimated and confined within the volume, sensible precautions include avoiding the unnecessary presence of personnel near the apparatus during operation.

To that end, the present invention is therefore also directed to a room comprising a radiotherapy apparatus as described hereinbefore, a security system comprising at least one door connected to a locking arrangement, wherein the security system is adapted to set the locking arrangement to allow or deny access to the room.

The room security system may be connected to the controller. The security system may comprise a locking arrangement to selectively allow or deny entry to the room in which the radiotherapy apparatus is located. Thus, at the end of a working day for example—staff could ensure that the room is clear of personnel and ferromagnetic items and any other objects which should not be present during operation of the radiotherapy apparatus, leave the room and subsequently put the locking arrangement into a state in which (subsequent) entry is denied. If the locking arrangement does not allow entry into the room before a later calibration process begins, then the state of the room is known to be safe and so steps (i) to (iv) can be carried out. Only once the calibration method has been completed would the locking arrangement be put into a state in which entry into the room is allowed. Alternatively, or in addition, the state of the or each door into the room can be monitored by the security system; if the or each door has not been opened since receipt of a confirmation that the room was clear, then it can be inferred that the room is still clear.

The step (b) of carrying out safety checks in the method above may comprise the steps of confirming whether a user ensured that the room was absent of personnel and ferromagnetic items at a particular point in time, and confirming whether entry to the room has been denied since.

The radiotherapy apparatus or room may further comprise an override system connected to the controller. In the case of an emergency, such as a door being forced open or it being discovered that the room is not free of personnel or ferromagnetic items, the override system can bring the calibration steps to a halt and deactivate the imaging and/or therapeutic radiation source.

The radiotherapy apparatus or room may further comprise monitoring devices connected to the controller, the monitoring devices providing information about one or more conditions of the radiotherapy apparatus. Thus, if any conditions of the radiotherapy apparatus vary outside a predetermined range then the override system may be activated automatically.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
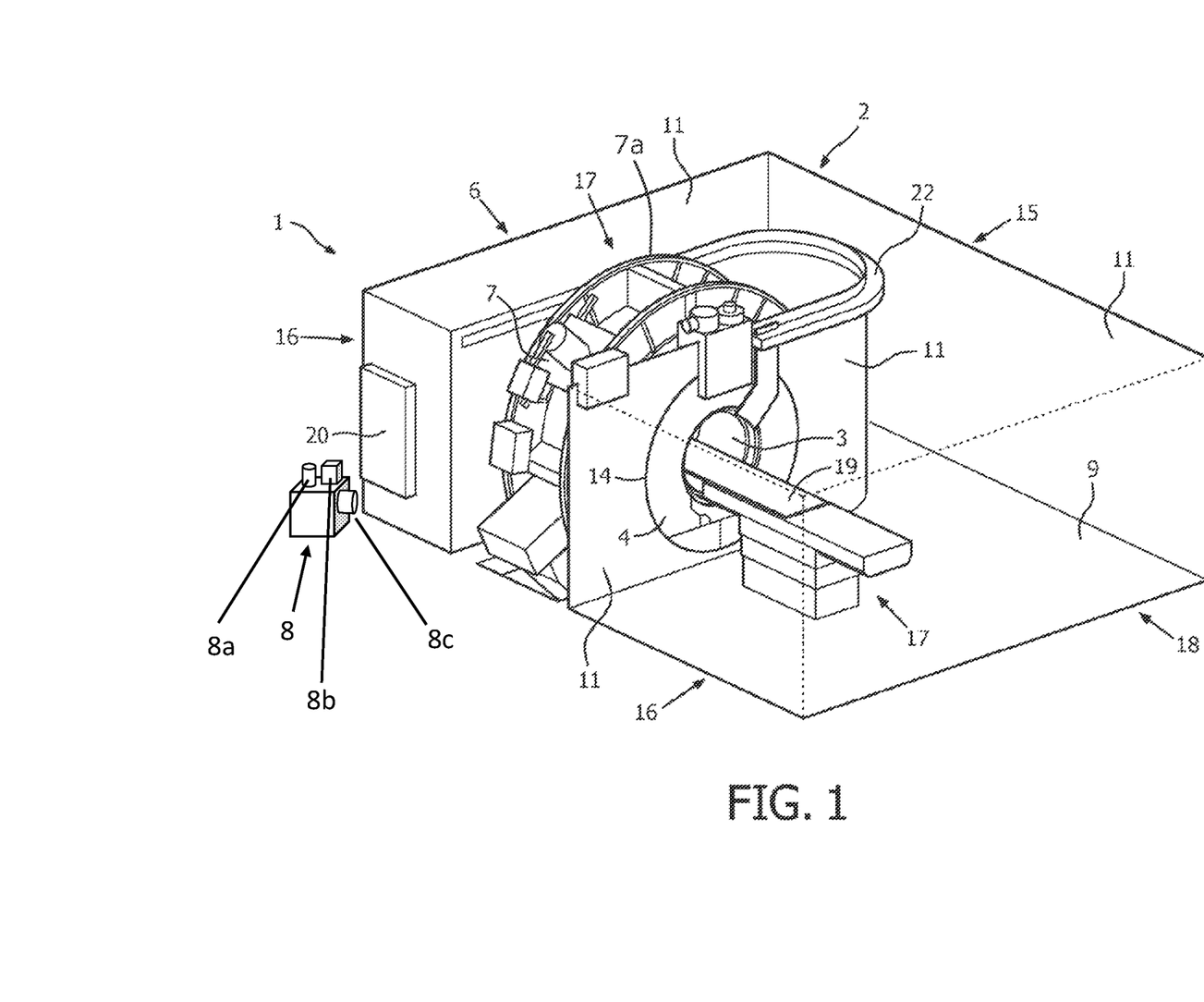
FIG. 1 shows a perspective view of an exam room of a magnetic resonance imaging system with an exam room shielding and an additional linac device according to a general setup, FIG. 2 schematically shows a detailed top view of the general exam room of FIG. 1 during a treatment, FIG. 3 schematically shows the top view of FIG. 2 during a calibration step.
Figure 2:
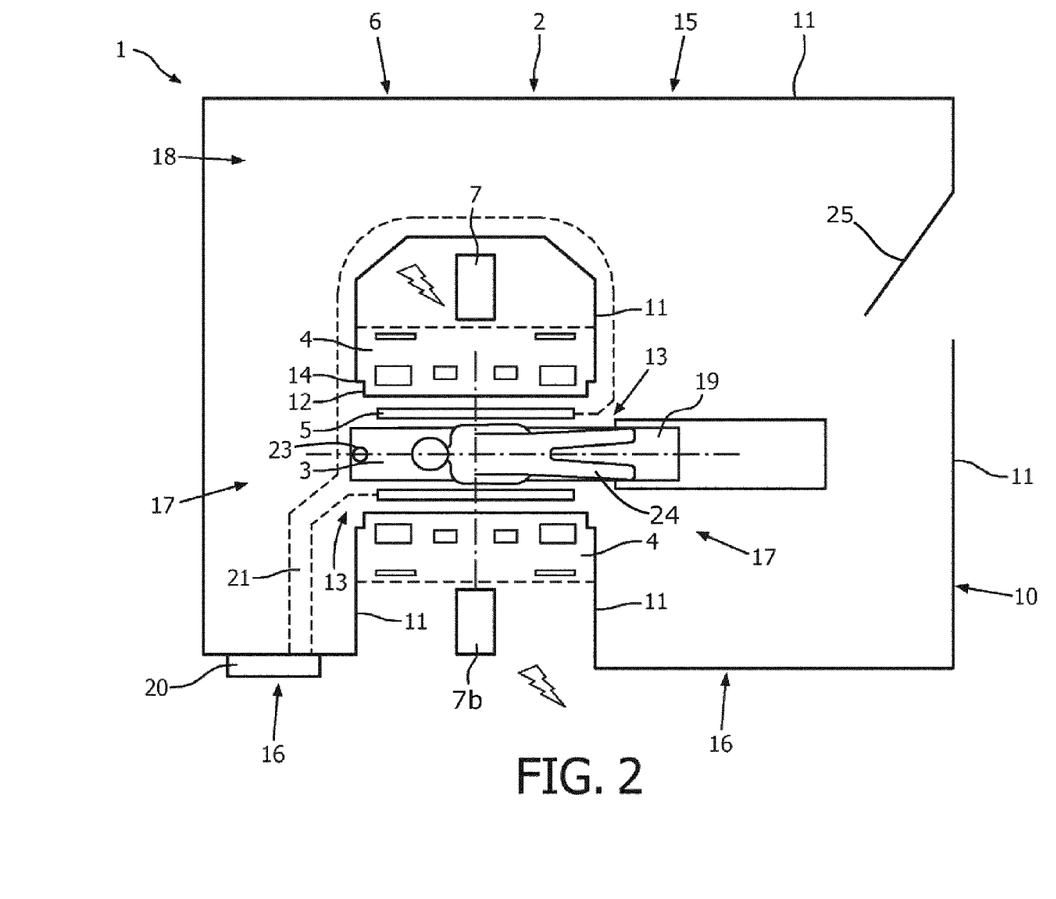

FIGS. 1 and 2 show the general setup of an examination room 1 of a combined magnetic resonance (MR) imaging system 2 and treatment system 6. The general setup of the MR imaging system 2 comprises an examination tube 3, a main magnet 4 and a gradient coil assembly 5, whereby the main magnet 4 and the gradient coil assembly 5 are located to surround the examination tube 3, as can be best seen in FIGS. 2 and 3. The treatment system 6 comprises a linac device 7 on a rotating gantry 7a, which is operated together with the MR imaging system 2. The linac device 7 is located at an outer circumference of the main magnet 4. A portal imaging device 7b is located on the gantry 7a, opposite the linac 7. The portal imaging device 7b captures an image of the therapeutic radiation emitted by the linac 7 after attenuation by a patient or other material between the linac 7 and the portal imager 7b.

The exam room 1 has an exam room shielding 10 for electromagnetically shielding the MR imaging system 2. Accordingly, the exam room shielding 10 is made of an electrically conductive material. The exam room shielding 10 comprises a ceiling, which is not shown in the figures, a floor 9 of the exam room 1, and side walls 11 interconnecting the ceiling and the floor 9. The side walls 11 of the exam room shielding 10 form the outline of a U-shaped room 15 with the longitudinal ends 13 of the examination tube 3 of the magnetic resonance imaging system 2 interconnecting the lateral flanks 16 of the U-shaped room 15.

The U-shaped room 15 is provided with operational spaces 17, which are located in front of the longitudinal ends 13 of the examination tube 3. The U-shaped room 15 is provided with a walkway 18 between the operational spaces 17, which is the base of the U-shaped room 15 in this embodiment. An examination table 19 is located inside the exam room shielding 10, so that a patient lying on this examination table 19, can be moved from one operational space 17 into the examination tube 3 and vice versa.

Figure 3:
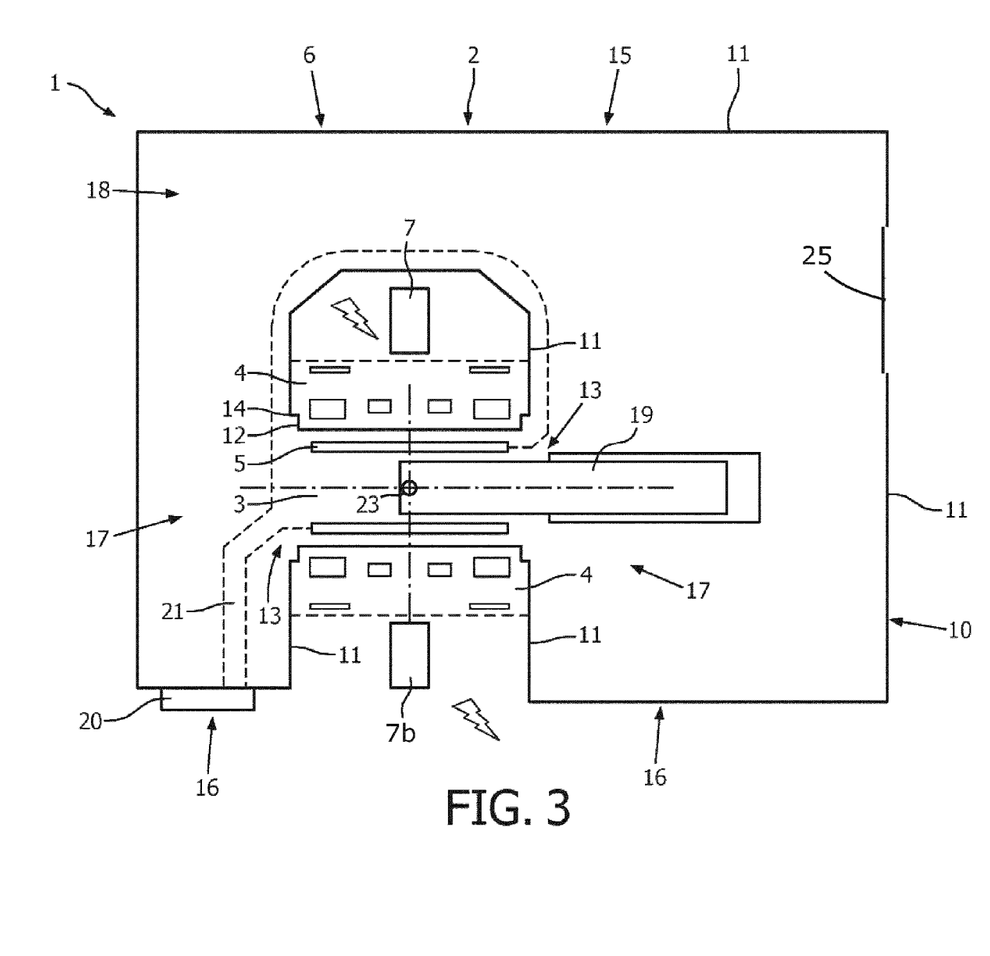

The exam room shielding 10 further comprises a filter box 20 for through connection of electric cables 21. The electric cables 21 are amongst others connected to the gradient coil assembly 5 at both longitudinal ends 13 of the examination tube 3, as schematically shown in FIGS. 2 and 3. As can be seen in FIG. 1, the exam room shielding 10 comprises a cable duct 22, which is arranged within an inner space of the exam room shielding 10 along a side wall 11 thereof. The cable duct 22 interconnects the longitudinal ends 13 of the examination tube 3.

An access door 25 allows ingress and egress of patients and staff, and also includes shielding material in order to complete the Faraday cage around the apparatus. Normally closed in use, it is shown open in FIG. 2 for illustration.

The exam room shielding 10 further comprises a tubular shielding device 12, which is arranged to surround the examination tube 3 and the gradient coil assembly 5. The tubular shielding device 12 is made of an electrically conductive material as RF shield. The main magnet 4 and the linac device 7 are located at an outer circumference of the tubular shielding device 12. Both longitudinal ends 13 of the tubular shielding device 12 are circumferentially connected to openings 14 of the side walls 11 to provide an electrically conductive connection therebetween. Accordingly, a fully shielded compartment is formed within the exam room 1, where the examination tube 3 and the gradient coil assembly 5 as well as cables 21 are shielded from the main magnet 4 and the linac device 7.

FIG. 2 shows the apparatus in a treatment position. The examination table 19 includes a set of calibration markers 23 (shown schematically) which may be of any known design, suitable for resolution in MRI and x-ray images. Such markers are often integrated into a "phantom", a discrete device that can be placed on an examination table 19 for test purposes. In this embodiment, however, the calibration markers 23 are integrated into an end portion of the examination table 19. The table 19 is sufficiently long that during the treatment process illustrated in FIG. 2, the calibration markers 23 project through the examination tube 3 and out of its distal end. The patient 24 is able to lie on a section of couch toward the centre of the examination table 19 which does not overlap with the calibration markers 23. Visual indicia may be provided on the examination table 19 to assist with positioning the patient in this way.

This places the calibration markers 23 out of the treatment field of the linac 7 and out of the imaging field of the MRI imaging system 2. As a result, the material of the calibration markers 23 will not scatter x-radiation produced by the linac 7 and will not affect imaging by the MRI system 2. It is not necessary as such for the calibration markers to extend completely outside the examination tube 3, simply to be positioned outside the treatable volume of the linac 7 and, preferably, also the imageable volume of the MRI system 2.

FIG. 3 shows a calibration phase. With the door 25 closed, the examination table 19 is moved into a fully-retracted position so that the calibration markers 23 are placed substantially at the isocentre, i.e. at the centre point of the treatable volume of the linac 7 and of the imaging volume of the MRI system 2. If the calibration markers are embedded at a different location in the examination table 19, then the table 19 should be located accordingly. The MRI imaging system 2 and the linac 7 and portal imager 7b are then operated so as to obtain images from both systems. These will both illustrate the calibration markers 23, which will allow spatial registration of the two systems. Portal images are often of a relatively poor quality, with little contrast between tissue types, but will be more than adequate for accurate positional imaging of calibration markers containing appropriately chosen materials. A comparison can be made between 2D slices from the MRI system and corresponding 2D projection images from the portal imaging system, or between a 3D dataset from the MRI system and a 3D portal-CT dataset, or otherwise, as required.

If the registration vector between the two systems is beyond a preset limit, or has changed significantly since the previous calibration check, then an alert signal can be passed to the operator.

Figure 4:
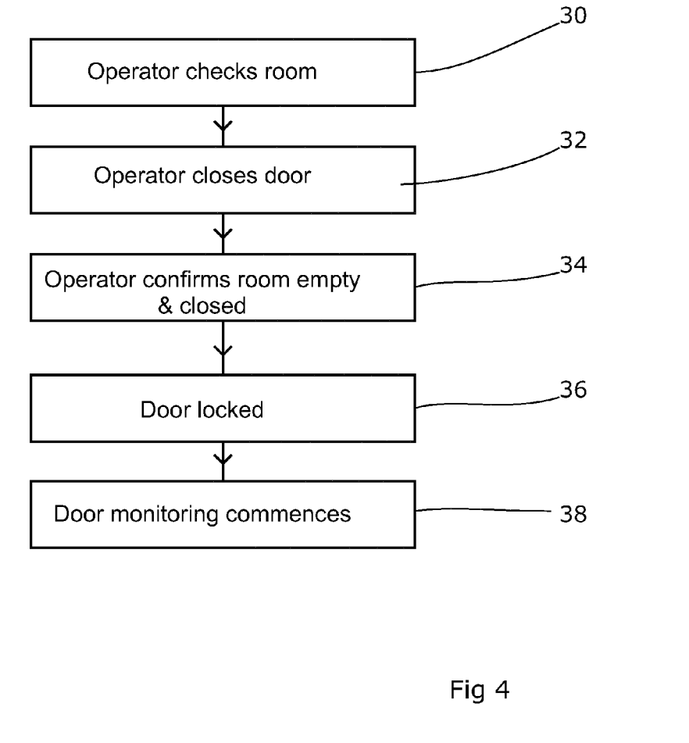
FIGS. 4 and 5 show a flowcharts for the stages of the calibration process.
Figure 5:
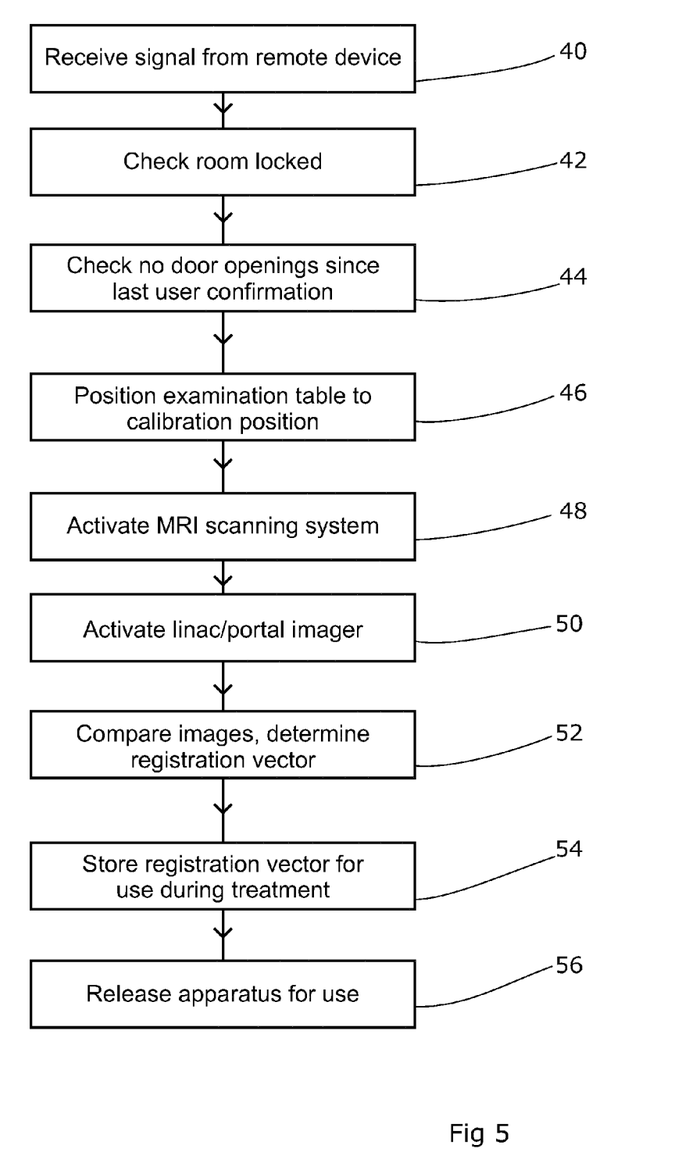

Thus, FIGS. 4 and 5 show flowcharts for the calibration process. FIG. 4 shows a flowchart for the end of an operational day, calling at step 30 for the operator to check the room 1 to ensure it is clear of patients, staff, and ferro magnetic objects and thus safe to run an automated calibration check. The operator then leaves the door 25 in the closed state (step 32) and confirms to the apparatus control unit (shown at 8 in FIG. 1) that the room is clear and closed (step 34). The control unit can then lock the door 25 via the security system (step 36). Alternatively, the operator could lock the door manually. Optionally, the security system can begin to monitor the door state to check for it being opened (step 38); this will be particularly useful if the lock is a manual one.

FIG. 5 shows the process as it resumes prior to a subsequent operational day, such as the following morning. The operator can log in to the control unit remotely, via a direct point-to-point connection, or a web portal, or a mobile app, or the like, and initiate a calibration process (step 40). The control unit will check that the room is still locked (step 42) and that the door has not been opened (step 44) since the operator confirmed that the room was clear (step 34). If these are true then the control unit can safely assume that the room is still clear and that it is safe to move objects and activate the various systems. The control unit therefore commands the examination table to move to the calibration position shown in FIG. 3 (step 46) and activates the MRI scanning system (step 48) and the portal imaging system (step 50). These may be activated simultaneously or sequentially. Once images are available from both systems, these are compared (step 52) and the registration vector determined. This shows the difference in spatial calibration between the two systems and may include translational and/or rotational elements. If this is outside tolerance, or has changed since the last calibration by an excessive amount, then a warning may be sounded and/or service attention sought. Assuming all is well, the vector will be stored for use in the day's operational activities (step 54), and the apparatus released for use (step 56) by (for example) unlocking the door 25.

If the control unit is accessible via an app or web portal, then this allows for a wide range of useful functions. For example, if the control unit knows that the room is in a closed and safe state, it can be set to send out a communication to the operator at a convenient time (such as an hour before the first treatment session is due to start) via a module for connection 8a to ask if the operator would like the system to begin a calibration process. It could also send a message if the room is not left in a safe and closed state, to let the operator know that they will not be able to initiate calibration. The interface could show live status updates of the apparatus or a group of apparatuses, showing their current status such as safe/not-safe, open/closed, running calibration, treating a patient etc so that the operator can be aware of use is being made of the apparatus and what the apparatus is available for. An override module 8b can be connected to the control unit 10, as are one or more monitoring devices 8c.

It will of course be understood that many variations may be made to the above-described embodiment without departing from the scope of the present invention.

The invention claimed is:
1. A radiotherapy apparatus, comprising:
 a source of therapeutic radiation and a magnetic resonance imaging system, both directed toward a common volume at a static predetermined location;
 a portal imaging device for the therapeutic radiation;
 a patient support, incorporating calibration markers integrated in the patient support and located at or towards one end of the patient support; and
 a controller;
 wherein the calibration markers are resolvable in both the magnetic resonance imaging system and the portal imaging device, and are fixed in a pre-determined position relative to the patient support, wherein, the patient support is moveable relative to the common volume, to an extent sufficient to bring the calibration markers selectively into and out of the common volume, and wherein the controller is configurable to recurrently initiate a calibration process comprising at least the steps of:

moving the patient support to a position in which the calibration markers are within the common volume; and obtaining an image from both the magnetic resonance imaging system and the portal imaging device.

2. The radiotherapy apparatus according to claim 1, wherein the calibration markers comprise at least one object of a material capable of appearing in the image produced by the magnetic resonance imaging system, and at least one object of a material capable of appearing in the image produced by the portal imaging device, the at least one objects being fixed in a pre-determined position relative to the calibration markers.

3. The radiotherapy apparatus according to claim 1, wherein the controller is configurable to move the patient support to a position in which the calibration markers are outside the common volume, prior to a treatment phase.

4. The radiotherapy apparatus according to claim 1, wherein the patient support includes a central section into which the calibration markers does not extend.

5. The radiotherapy apparatus according to claim 1, wherein the controller further comprises a module for connection to an outside communication network.

6. The radiotherapy apparatus according to claim 1, further comprising an override module connected to the controller.

7. The radiotherapy apparatus according to claim 1, further comprising one or more monitoring devices connected to the controller.

8. The radiotherapy apparatus according to claim 1, in combination with a room, and a security system comprising at least one door connected to a locking arrangement, wherein the security system is adapted to set the locking arrangement to allow or deny access to the room.

9. The radiotherapy apparatus according to claim 8 in which the security system is connected to the controller of the radiotherapy apparatus.

10. The radiotherapy apparatus according to claim 8, the room further comprising one or more monitoring devices connected to the controller, the one or more monitoring devices providing information about one or more conditions of the radiotherapy apparatus.

11. A method of calibrating a radiotherapy apparatus, the radiotherapy apparatus comprising:

a source of therapeutic radiation and a magnetic resonance imaging system, both directed toward a common volume at a static predetermined location;

a portal imaging device for the therapeutic radiation; and a patient support, including calibration markers integrated in the patient support and located at or towards one end of the patient support;

wherein the calibration markers are resolvable in both the magnetic resonance imaging system and the portal imaging device, and are fixed in a pre-determined position relative to the patient support, and wherein the calibration method comprising the steps of:

(i.) moving the patient support relative to the common volume to an extent sufficient to place the calibration markers within the common volume;

(ii.) obtaining an image from both the magnetic resonance imaging system and the portal imaging device;

(iii.) spatially correlating the magnetic resonance imaging system and the portal imaging device on the basis of the respective images; and (iv.) moving the patient support relative to the common volume to an extent sufficient to place the calibration markers outside the common volume.

12. The method according to claim 11, wherein the step of moving the patient support relative to the common volume to an extent sufficient to place the calibration markers within the common volume comprises moving the patient support to a pre-determined position.

13. The method according to claim 11, wherein a control unit is provided, adapted to carry out a method comprising the steps of:

a) receiving an activation signal from a remote communication device;

b) carrying out one or more safety checks;

c) performing steps (i) to (iv); and d) providing a confirmation signal to a remote communication device.

14. The method according to claim 13, wherein the one or more safety checks of step (b) comprise the steps of confirming whether a user has ensured that a room containing the radiotherapy apparatus was absent of personnel and/or ferromagnetic items at a particular point in time.

15. The method according to claim 14, wherein the one or more safety checks of step (b) further comprise the step of confirming that, at least one of entry to the room has been denied or no entry has been made into the room, since receiving user confirmation.

16. The method according to claim 11, comprising an override step capable of bringing the calibration steps to a halt and deactivating the imaging and/or therapeutic radiation source.

17. The radiotherapy apparatus according to claim 1, wherein the patient support is a patient table.

18. The method according to claim 11, wherein the patient support is a patient table.

* * * * *